US010246500B2

(12) United States Patent
Barth et al.

(10) Patent No.: US 10,246,500 B2
(45) Date of Patent: Apr. 2, 2019

(54) HUMAN CYTOLYTIC FUSION PROTEINS

(71) Applicant: University of Cape Town, Cape Town (ZA)

(72) Inventors: Stefan Barth, Cape Town (ZA); Thomas Nachreiner, Inden (DE); Christian Cremer, Aachen (DE)

(73) Assignee: The University of Cape Town, Cape Town (ZA)

( * ) Notice: Subject to any disclaimer, the term of this patent is extended or adjusted under 35 U.S.C. 154(b) by 0 days.

(21) Appl. No.: 15/318,584

(22) PCT Filed: Jun. 15, 2015

(86) PCT No.: PCT/EP2015/063282
§ 371 (c)(1),
(2) Date: Dec. 13, 2016

(87) PCT Pub. No.: WO2015/189427
PCT Pub. Date: Dec. 17, 2015

(65) Prior Publication Data
US 2017/0114111 A1 Apr. 27, 2017

Related U.S. Application Data

(60) Provisional application No. 62/011,921, filed on Jun. 13, 2014.

(30) Foreign Application Priority Data

Jun. 13, 2014 (EP) .................................... 14172288

(51) Int. Cl.
C07K 14/515 (2006.01)
C07K 16/28 (2006.01)
A61K 38/18 (2006.01)
A61K 38/00 (2006.01)

(52) U.S. Cl.
CPC ........ *C07K 14/515* (2013.01); *A61K 38/1891* (2013.01); *C07K 16/28* (2013.01); *C07K 16/283* (2013.01); *A61K 38/00* (2013.01); *C07K 2317/622* (2013.01); *C07K 2319/00* (2013.01); *C07K 2319/74* (2013.01)

(58) Field of Classification Search
CPC .... A61K 38/16; A61K 38/18; A61K 38/1891; C07K 14/51; C07K 14/515; C07K 16/283; C07K 16/28; C07K 2319/00; C07K 2319/74
See application file for complete search history.

(56) References Cited

U.S. PATENT DOCUMENTS 4,946,778 A 8/1990 Ladner et al.
2017/0369574 A1* 12/2017 Barth .................... C07K 16/283

FOREIGN PATENT DOCUMENTS

WO 2011/062762 A2 5/2011

OTHER PUBLICATIONS

Hristodorov, Dmitrij, "CD64-Mediated Specific Elimination of M1-Polarized Macrophages—Implications for Therapeutic Intervention in Chronic Inflammatory Diseases." Doctoral Thesis, 2013, RWTH Aachen, http://darwin.bth.rwth-aachen.de/opus/volltexte/2013/4705/.
Stahnke et al. "Granzyme B-H22(scFv), A Human Immunotoxin Targeting CF64 in Acute Myeloid Leukemia of Monocytic Subtypes." Molecular Cancer Therapeutics, Sep. 2008, 7(9)2924-2932, American Association for Cancer Research.
Krauss et al. "Targeting Malignant B-cell Lymphoma with a Humanized Anti-CD22 scFv-Angiogenin Immunoenzyme." Br J Haematol, 2005, 128(5)602-609. Blackwell Publishing Ltd.
Schiffer et al. "Species-Dependent Functionality of the Human Cytolytic Fusion Proteins Granzyme B-H22(scFv) and H22(scFv)-Angiogenin in Macrophages." Antibodies, 2013, 2(1)9-18.
De Lorenzo et al. "Intracellular Route and Mechanism of Action of ERB-hRNase, a Human Anti-ErbB2 Anticancer Immunoagent." Federation of European Biochemical Sciences, 2007, 581(2)296-300. Elsevier B.V.
Schirrmann et al. "Evaluation of Human Pancreatic RNase as Effector Molecule in a Therapeutic Antibody Platform." MAbs, 2014, 6(2)367-380, Landes Bioscience.
Huston et al. "Protein Engineering of Antibody Binding Sites: Recovery of Specific Activity in an Anti-Digoxin Single-Chain Fv Analogue Produced in *Escherichia coli*." Proc. Natl. Acad. Sci. USA, Aug. 1988, 85:5879-5883, Biochemistry.
Russo et al. "Role of Glutamine-117 in the Ribonucleolytic Activity of Human Angiogenin". Proc. Natl. Acad. Sci. USA, Apr. 1994, 91(8)2920-2924; Biochemistry.
Gallagher et al. "Characterization of the Continuous, Differentiating Myeloid Cell Line (HL-60) From a Patient with Acute Promyelocytic Leukemia." Blood Journal, Sep. 1979, 54(3)713-733.
Bovolenta et al. "High Affinity Receptor for IgG (FcGammaRI/CD64) Gene and STAT Protein Binding to the IFN-Gamma Response Region (GRR) are Regulated Differentially in Human Neutrophils and Monocytes by IL-10." J Immunol, 1998, 160(2)911-919.
Zhong et al. "Cytotoxicity of Anti-CD64-Ricin A Chain Immunotoxin Against Human Acute Myeloid Leukemia Cells in Vitro and in SCID Mice." Journal of Hematotherapy & Stem Cell Research, 2001, 10(1)95-105.

(Continued)

*Primary Examiner* — Karen Cochrane Carlson
(74) *Attorney, Agent, or Firm* — Wagenknecht IP Law Group PC

(57) ABSTRACT

The technology provided herein relates to novel human cytolytic fusion proteins (hCFPs) suitable to induce apoptosis in human cells comprising a target cell-specific binding component and a human effector domain, wherein the binding component comprises an antibody or an antibody fragment with an antigen-binding site for binding to the cellular surface receptor CD64 and the effector domain comprises a variant of wild type human angiogenin (Ang) or a functional fragment thereof; to nucleic acid molecules encoding said recombinant hCFPs, vectors and host cells containing said nucleic acids and methods for preparation and producing these hCFPs.

20 Claims, 8 Drawing Sheets

Figure 1:
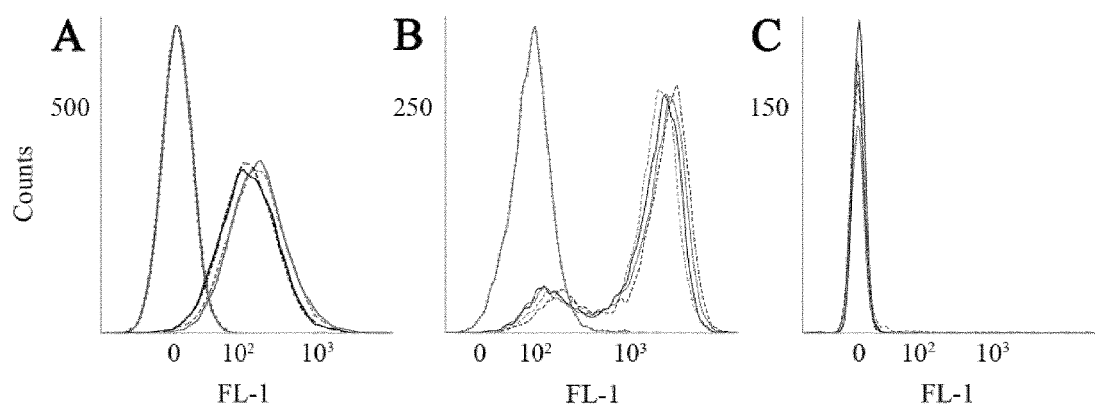

Specification includes a Sequence Listing.

(56) References Cited

OTHER PUBLICATIONS

Stoecker et al. "Secretion of Functional Anti-CD 30-Angiogenin Immunotoxins into the Supernatant of Transfected 293T-cells." Protein Expression and Purification, 2003, 28(2)211-219, El Sevier.

Ribbert et al. "Recombinant, ETA-based CD64 Immunotoxins: Improved Efficacy by Increased Valency, Both In Vitro and In Vivo in a Chronic Cutaneous Inflammation Model in Human CD64 Transgenic Mice." British Journal of Dermatology, 2010, 163(2)279-286.

Verhoven et al. "Mechanisms of Phosphatidylserine Exposure, A Phagocyte Recognition Signal, on Apoptotic T Lymphocytes." J. Exp. Med., Nov. 1, 1995, 182:1597-1601, The Rockefeller University Press.

Stoecker et al. "Eukaryotic Expression and Secretion of EGFP-Labeled Annexin A5." Protein Expression and Purification, 2008, 58(2)325-331, El Sevier.

Huhn et al. "Human Angiogenin Fused to Human CD30 Ligand (Ang-CD30L) Exhibits Specific Cytotoxicity Against CD30-Positive Lymphoma." Cancer Research, Dec. 15, 2001, 61(24)8737-8742

Diehl et al. "Hodgkin's Disease: Establishment and Characterization of Four In Vitro Cell Lines." J Cancer Res Clin Oncol, 1981, 101(1)111-124, Springer-Verlag.

PCT/EP2015/063282 International Search Report dated Oct. 2, 2015.

Berges et al. "Human Cytolytic Fusion Proteins: Modified Versions of Human Granzyme B and Angiogenin Have the Potential to Replace Bacterial Toxins in Targeted Therapies Against CD64+ Diseases." Antibodies, Feb. 19, 2014, 3(1)92-115.

Hetzel et al. "Small Cleavable Adapters Enhance the Specific Cytotoxicity of a Humanized Immunotoxin Directed Against CD64-Positive Cells." Journal of Immunotherapy, May 1, 2008, 31(4)370-376, Lippincott Wlllliams & Wilkins.

Stoecker, et al. "Secretion of Functional Anti-CD30-Angiogenin Immunotoxins into the Supernatant of Transfected 293T-Cells." Protein Expression and Purification, Apr. 1, 2003, 28(2)211-219; Academic Press.

* cited by examiner

FIGURE 6

Human wild-type angiogenin amino acid sequence without leader sequence (SEQ ID NO.1)

```
1     QDNSRYTHFL TQHYDAKPQG RDDRYCESIM RRRGLTSPCK DINTFIHGNK RSIKAICENK
61    NGNPHRENLR ISKSSFQVTT CKLHGGSPWP PCQYRATAGF RNVVVACENG LPVHLDQSIF
121   RRP
```

FIGURE 7

H22-Ang WT sequence (SEQ ID NO.2)

| | |
|---|---|
| 1 | DAAQPAMAQV QLVESGGGVV QPGRSLRLSC SSSGFIFSDN YMYWVRQAPG KGLEWVATIS |
| 61 | DGGSYTYYPD SVKGRFTISR DNSKNTLFLQ MDSLRPEDTG VYFCARGYYR YEGAMDYWGQ |
| 121 | GTPVTVSSGG GGSGGGGSGG GGSDIQLTQS PSSLSASVGD RVTITCKSSQ SVLYSSNQKN |
| 181 | YLAWYQQKPG KAPKLLIYWA STRESGVPSR FSGSGSGTDF TFTISSLQPE DIATYYCHQY |
| 241 | LSSWTFGQGT KLEIKAAALE SRQDNSRYTH FLTQHYDAKP QGRDDRYCES IMRRRGLTSP 301 |
| | CKDINTFIHG NKRSIKAICE NKNGNPHREN LRISKSSFQV TTCKLHGGSP WPPCQYRATA |
| 361 | GFRNVVVACE NGLPVHLDQS IFRRPAEHEF RGGPEQKLIS EEDLNSAVDH HHHHH |

H22-Ang GGRR<sub>mut</sub> sequence (SEQ ID NO.3)

| | |
|---|---|
| 1 | DAAQPAMAQV QLVESGGGVV QPGRSLRLSC SSSGFIFSDN YMYWVRQAPG KGLEWVATIS |
| 61 | DGGSYTYYPD SVKGRFTISR DNSKNTLFLQ MDSLRPEDTG VYFCARGYYR YEGAMDYWGQ |
| 121 | GTPVTVSSGG GGSGGGGSGG GGSDIQLTQS PSSLSASVGD RVTITCKSSQ SVLYSSNQKN |
| 181 | YLAWYQQKPG KAPKLLIYWA STRESGVPSR FSGSGSGTDF TFTISSLQPE DIATYYCHQY |
| 241 | LSSWTFGQGT KLEIKAAALE SRQDNSRYTH FLTQHYDAKP QGRDDRYCES IMRRRGLTSP 301 |
| | CKDINTFIHG NKRSIKAICE NKNGNPHREN LRISKSSFQV TTCKLHRRSP WPPCQYRATA |
| 361 | GFRNVVVACE NGLPVHLDQS IFRRPAEHEF RGGPEQKLIS EEDLNSAVDH HHHHH |

H22-Ang QG<sub>mut</sub> sequence (SEQ ID NO.4)

| | |
|---|---|
| 1 | DAAQPAMAQV QLVESGGGVV QPGRSLRLSC SSSGFIFSDN YMYWVRQAPG KGLEWVATIS |
| 61 | DGGSYTYYPD SVKGRFTISR DNSKNTLFLQ MDSLRPEDTG VYFCARGYYR YEGAMDYWGQ |
| 121 | GTPVTVSSGG GGSGGGGSGG GGSDIQLTQS PSSLSASVGD RVTITCKSSQ SVLYSSNQKN |
| 181 | YLAWYQQKPG KAPKLLIYWA STRESGVPSR FSGSGSGTDF TFTISSLQPE DIATYYCHQY |
| 241 | LSSWTFGQGT KLEIKAAALE SRQDNSRYTH FLTQHYDAKP QGRDDRYCES IMRRRGLTSP 301 |
| | CKDINTFIHG NKRSIKAICE NKNGNPHREN LRISKSSFQV TTCKLHGGSP WPPCQYRATA |
| 361 | GFRNVVVACE NGLPVHLDGS IFRRPAEHEF RGGPEQKLIS EEDLNSAVDH HHHHH |

H22-Ang GGRR/QG<sub>mut</sub> sequence (SEQ ID NO.5)

| | |
|---|---|
| 1 | DAAQPAMAQV QLVESGGGVV QPGRSLRLSC SSSGFIFSDN YMYWVRQAPG KGLEWVATIS |
| 61 | DGGSYTYYPD SVKGRFTISR DNSKNTLFLQ MDSLRPEDTG VYFCARGYYR YEGAMDYWGQ |
| 121 | GTPVTVSSGG GGSGGGGSGG GGSDIQLTQS PSSLSASVGD RVTITCKSSQ SVLYSSNQKN |
| 181 | YLAWYQQKPG KAPKLLIYWA STRESGVPSR FSGSGSGTDF TFTISSLQPE DIATYYCHQY |

FIGURE 7 (continued)

241 LSSWTFGQGT KLEIKAAALE SRQDNSRYTH FLTQHYDAKP QGRDDRYCES IMRRRGLTSP 301
    CKDINTFIHG NKRSIKAICE NKNGNPHREN LRISKSSFQV TTCKLHRRSP WPPCQYRATA
361 GFRNVVVACE NGLPVHLDGS IFRRPAEHEF RGGPEQKLIS EEDLNSAVDH HHHHH

SEQUENCE LISTING

```
<160> NUMBER OF SEQ ID NOS: 9

<210> SEQ ID NO 1
<211> LENGTH: 123
<212> TYPE: PRT
<213> ORGANISM: Homo sapiens

<400> SEQUENCE: 1

Gln Asp Asn Ser Arg Tyr Thr His Phe Leu Thr Gln His Tyr Asp Ala
1               5                   10                  15

Lys Pro Gln Gly Arg Asp Arg Tyr Cys Glu Ser Ile Met Arg Arg
            20                  25                  30

Arg Gly Leu Thr Ser Pro Cys Lys Asp Ile Asn Thr Phe Ile His Gly
        35                  40                  45

Asn Lys Arg Ser Ile Lys Ala Ile Cys Glu Asn Lys Asn Gly Asn Pro
    50                  55                  60

His Arg Glu Asn Leu Arg Ile Ser Lys Ser Ser Phe Gln Val Thr Thr
65                  70                  75                  80

Cys Lys Leu His Gly Gly Ser Pro Trp Pro Pro Cys Gln Tyr Arg Ala
                85                  90                  95

Thr Ala Gly Phe Arg Asn Val Val Val Ala Cys Glu Asn Gly Leu Pro
            100                 105                 110

Val His Leu Asp Gln Ser Ile Phe Arg Arg Pro
        115                 120

<210> SEQ ID NO 2
<211> LENGTH: 415
<212> TYPE: PRT
<213> ORGANISM: Artificial Sequence
<220> FEATURE:
<223> OTHER INFORMATION: Fusionprotein H22-Ang WT

<400> SEQUENCE: 2

Asp Ala Ala Gln Pro Ala Met Ala Gln Val Gln Leu Val Glu Ser Gly
1               5                   10                  15

Gly Gly Val Val Gln Pro Gly Arg Ser Leu Arg Leu Ser Cys Ser Ser
            20                  25                  30

Ser Gly Phe Ile Phe Ser Asp Asn Tyr Met Tyr Trp Val Arg Gln Ala
        35                  40                  45
```

```
Pro Gly Lys Gly Leu Glu Trp Val Ala Thr Ile Ser Asp Gly Gly Ser
 50                  55                  60

Tyr Thr Tyr Tyr Pro Asp Ser Val Lys Gly Arg Phe Thr Ile Ser Arg
 65                  70                  75                  80

Asp Asn Ser Lys Asn Thr Leu Phe Leu Gln Met Asp Ser Leu Arg Pro
                 85                  90                  95

Glu Asp Thr Gly Val Tyr Phe Cys Ala Arg Gly Tyr Tyr Arg Tyr Glu
            100                 105                 110

Gly Ala Met Asp Tyr Trp Gly Gln Gly Thr Pro Val Thr Val Ser Ser
            115                 120                 125

Gly Gly Gly Gly Ser Gly Gly Gly Gly Gly Gly Ser Gly Gly Ser Asp
        130                 135                 140

Ile Gln Leu Thr Gln Ser Pro Ser Ser Leu Ser Ala Ser Val Gly Asp
145                 150                 155                 160

Arg Val Thr Ile Thr Cys Lys Ser Ser Gln Ser Val Leu Tyr Ser Ser
                165                 170                 175

Asn Gln Lys Asn Tyr Leu Ala Trp Tyr Gln Gln Lys Pro Gly Lys Ala
            180                 185                 190

Pro Lys Leu Leu Ile Tyr Trp Ala Ser Thr Arg Glu Ser Gly Val Pro
        195                 200                 205

Ser Arg Phe Ser Gly Ser Gly Thr Asp Phe Thr Phe Thr Ile
210                 215                 220

Ser Ser Leu Gln Pro Glu Asp Ile Ala Thr Tyr Tyr Cys His Gln Tyr
225                 230                 235                 240

Leu Ser Ser Trp Thr Phe Gly Gln Gly Thr Lys Leu Glu Ile Lys Ala
                245                 250                 255

Ala Ala Leu Glu Ser Arg Gln Asp Asn Ser Arg Tyr Thr His Phe Leu
            260                 265                 270

Thr Gln His Tyr Asp Ala Lys Pro Gln Gly Arg Asp Asp Arg Tyr Cys
        275                 280                 285

Glu Ser Ile Met Arg Arg Arg Gly Leu Thr Ser Pro Cys Lys Asp Ile
290                 295                 300

Asn Thr Phe Ile His Gly Asn Lys Arg Ser Ile Lys Ala Ile Cys Glu
305                 310                 315                 320

Asn Lys Asn Gly Asn Pro His Arg Glu Asn Leu Arg Ile Ser Lys Ser
                325                 330                 335

Ser Phe Gln Val Thr Thr Cys Lys Leu His Gly Gly Ser Pro Trp Pro
            340                 345                 350

Pro Cys Gln Tyr Arg Ala Thr Ala Gly Phe Arg Asn Val Val Val Ala
        355                 360                 365

Cys Glu Asn Gly Leu Pro Val His Leu Asp Gln Ser Ile Phe Arg Arg
370                 375                 380

Pro Ala Glu His Glu Phe Arg Gly Gly Pro Glu Gln Lys Leu Ile Ser
385                 390                 395                 400

Glu Glu Asp Leu Asn Ser Ala Val Asp His His His His His
                405                 410                 415

<210> SEQ ID NO 3
<211> LENGTH: 415
<212> TYPE: PRT
<213> ORGANISM: Artificial Sequence
<220> FEATURE:
<223> OTHER INFORMATION: Fusionprotein H22-Ang GGRRmut

<400> SEQUENCE: 3
```

```
Asp Ala Ala Gln Pro Ala Met Ala Gln Val Gln Leu Val Glu Ser Gly
1               5                   10                  15

Gly Gly Val Val Gln Pro Gly Arg Ser Leu Arg Leu Ser Cys Ser Ser
            20                  25                  30

Ser Gly Phe Ile Phe Ser Asp Asn Tyr Met Tyr Trp Val Arg Gln Ala
        35                  40                  45

Pro Gly Lys Gly Leu Glu Trp Val Ala Thr Ile Ser Asp Gly Gly Ser
    50                  55                  60

Tyr Thr Tyr Tyr Pro Asp Ser Val Lys Gly Arg Phe Thr Ile Ser Arg
65              70                  75                  80

Asp Asn Ser Lys Asn Thr Leu Phe Leu Gln Met Asp Ser Leu Arg Pro
                85                  90                  95

Glu Asp Thr Gly Val Tyr Phe Cys Ala Arg Gly Tyr Tyr Arg Tyr Glu
            100                 105                 110

Gly Ala Met Asp Tyr Trp Gly Gln Gly Thr Pro Val Thr Val Ser Ser
        115                 120                 125

Gly Gly Gly Gly Ser Gly Gly Gly Ser Gly Gly Gly Gly Ser Asp
            130                 135                 140

Ile Gln Leu Thr Gln Ser Pro Ser Ser Leu Ser Ala Ser Val Gly Asp
145                 150                 155                 160

Arg Val Thr Ile Thr Cys Lys Ser Ser Gln Ser Val Leu Tyr Ser Ser
            165                 170                 175

Asn Gln Lys Asn Tyr Leu Ala Trp Tyr Gln Gln Lys Pro Gly Lys Ala
                180                 185                 190

Pro Lys Leu Leu Ile Tyr Trp Ala Ser Thr Arg Glu Ser Gly Val Pro
            195                 200                 205

Ser Arg Phe Ser Gly Ser Gly Ser Gly Thr Asp Phe Thr Phe Thr Ile
        210                 215                 220

Ser Ser Leu Gln Pro Glu Asp Ile Ala Thr Tyr Tyr Cys His Gln Tyr
225                 230                 235                 240

Leu Ser Ser Trp Thr Phe Gly Gln Gly Thr Lys Leu Glu Ile Lys Ala
                245                 250                 255

Ala Ala Leu Glu Ser Arg Gln Asp Asn Ser Arg Tyr Thr His Phe Leu
            260                 265                 270

Thr Gln His Tyr Asp Ala Lys Pro Gln Gly Arg Asp Asp Arg Tyr Cys
        275                 280                 285

Glu Ser Ile Met Arg Arg Gly Leu Thr Ser Pro Cys Lys Asp Ile
290                 295                 300

Asn Thr Phe Ile His Gly Asn Lys Arg Ser Ile Lys Ala Ile Cys Glu
305                 310                 315                 320

Asn Lys Asn Gly Asn Pro His Arg Glu Asn Leu Arg Ile Ser Lys Ser
                325                 330                 335

Ser Phe Gln Val Thr Thr Cys Lys Leu His Arg Arg Ser Pro Trp Pro
            340                 345                 350

Pro Cys Gln Tyr Arg Ala Thr Ala Gly Phe Arg Asn Val Val Ala
        355                 360                 365

Cys Glu Asn Gly Leu Pro Val His Leu Asp Gln Ser Ile Phe Arg Arg
370                 375                 380

Pro Ala Glu His Glu Phe Arg Gly Gly Pro Glu Gln Lys Leu Ile Ser
385                 390                 395                 400

Glu Glu Asp Leu Asn Ser Ala Val Asp His His His His His
            405                 410                 415
```

<210> SEQ ID NO 4
<211> LENGTH: 415
<212> TYPE: PRT
<213> ORGANISM: Artificial Sequence
<220> FEATURE:
<223> OTHER INFORMATION: Fusionprotein H22-Ang QGmut

<400> SEQUENCE: 4

```
Asp Ala Ala Gln Pro Ala Met Ala Gln Val Gln Leu Val Glu Ser Gly
1               5                   10                  15

Gly Gly Val Val Gln Pro Gly Arg Ser Leu Arg Leu Ser Cys Ser Ser
            20                  25                  30

Ser Gly Phe Ile Phe Ser Asp Asn Tyr Met Tyr Trp Val Arg Gln Ala
        35                  40                  45

Pro Gly Lys Gly Leu Glu Trp Val Ala Thr Ile Ser Asp Gly Gly Ser
    50                  55                  60

Tyr Thr Tyr Tyr Pro Asp Ser Val Lys Gly Arg Phe Thr Ile Ser Arg
65                  70                  75                  80

Asp Asn Ser Lys Asn Thr Leu Phe Leu Gln Met Asp Ser Leu Arg Pro
                85                  90                  95

Glu Asp Thr Gly Val Tyr Phe Cys Ala Arg Gly Tyr Tyr Arg Tyr Glu
            100                 105                 110

Gly Ala Met Asp Tyr Trp Gly Gln Gly Thr Pro Val Thr Val Ser Ser
        115                 120                 125

Gly Gly Gly Gly Ser Gly Gly Gly Ser Gly Gly Gly Ser Asp
    130                 135                 140

Ile Gln Leu Thr Gln Ser Pro Ser Ser Leu Ser Ala Ser Val Gly Asp
145                 150                 155                 160

Arg Val Thr Ile Thr Cys Lys Ser Ser Gln Ser Val Leu Tyr Ser Ser
                165                 170                 175

Asn Gln Lys Asn Tyr Leu Ala Trp Tyr Gln Gln Lys Pro Gly Lys Ala
            180                 185                 190

Pro Lys Leu Leu Ile Tyr Trp Ala Ser Thr Arg Glu Ser Gly Val Pro
        195                 200                 205

Ser Arg Phe Ser Gly Ser Gly Ser Gly Thr Asp Phe Thr Phe Thr Ile
    210                 215                 220

Ser Ser Leu Gln Pro Glu Asp Ile Ala Thr Tyr Tyr Cys His Gln Tyr
225                 230                 235                 240

Leu Ser Ser Trp Thr Phe Gly Gln Gly Thr Lys Leu Glu Ile Lys Ala
                245                 250                 255

Ala Ala Leu Glu Ser Arg Gln Asp Asn Ser Arg Tyr Thr His Phe Leu
            260                 265                 270

Thr Gln His Tyr Asp Ala Lys Pro Gln Gly Arg Asp Asp Arg Tyr Cys
        275                 280                 285

Glu Ser Ile Met Arg Arg Gly Leu Thr Ser Pro Cys Lys Asp Ile
    290                 295                 300

Asn Thr Phe Ile His Gly Asn Lys Arg Ser Ile Lys Ala Ile Cys Glu
305                 310                 315                 320

Asn Lys Asn Gly Asn Pro His Arg Glu Asn Leu Arg Ile Ser Lys Ser
                325                 330                 335

Ser Phe Gln Val Thr Thr Cys Lys Leu His Gly Gly Ser Pro Trp Pro
            340                 345                 350

Pro Cys Gln Tyr Arg Ala Thr Ala Gly Phe Arg Asn Val Val Val Ala
        355                 360                 365
```

```
Cys Glu Asn Gly Leu Pro Val His Leu Asp Gly Ser Ile Phe Arg Arg
370                 375                 380

Pro Ala Glu His Glu Phe Arg Gly Gly Pro Glu Gln Lys Leu Ile Ser
385                 390                 395                 400

Glu Glu Asp Leu Asn Ser Ala Val Asp His His His His His His
                405                 410                 415

<210> SEQ ID NO 5
<211> LENGTH: 415
<212> TYPE: PRT
<213> ORGANISM: Artificial Sequence
<220> FEATURE:
<223> OTHER INFORMATION: Fusionprotein H22-Ang GGRR/QGmut

<400> SEQUENCE: 5

Asp Ala Ala Gln Pro Ala Met Ala Gln Val Gln Leu Val Glu Ser Gly
1               5                   10                  15

Gly Gly Val Val Gln Pro Gly Arg Ser Leu Arg Leu Ser Cys Ser Ser
                20                  25                  30

Ser Gly Phe Ile Phe Ser Asp Asn Tyr Met Tyr Trp Val Arg Gln Ala
            35                  40                  45

Pro Gly Lys Gly Leu Glu Trp Val Ala Thr Ile Ser Asp Gly Gly Ser
    50                  55                  60

Tyr Thr Tyr Tyr Pro Asp Ser Val Lys Gly Arg Phe Thr Ile Ser Arg
65                  70                  75                  80

Asp Asn Ser Lys Asn Thr Leu Phe Leu Gln Met Asp Ser Leu Arg Pro
                85                  90                  95

Glu Asp Thr Gly Val Tyr Phe Cys Ala Arg Gly Tyr Tyr Arg Tyr Glu
            100                 105                 110

Gly Ala Met Asp Tyr Trp Gly Gln Gly Thr Pro Val Thr Val Ser Ser
        115                 120                 125

Gly Gly Gly Gly Ser Gly Gly Gly Ser Gly Gly Gly Ser Asp
130                 135                 140

Ile Gln Leu Thr Gln Ser Pro Ser Ser Leu Ser Ala Ser Val Gly Asp
145                 150                 155                 160

Arg Val Thr Ile Thr Cys Lys Ser Ser Gln Ser Val Leu Tyr Ser Ser
                165                 170                 175

Asn Gln Lys Asn Tyr Leu Ala Trp Tyr Gln Gln Lys Pro Gly Lys Ala
            180                 185                 190

Pro Lys Leu Leu Ile Tyr Trp Ala Ser Thr Arg Glu Ser Gly Val Pro
    195                 200                 205

Ser Arg Phe Ser Gly Ser Gly Ser Gly Thr Asp Phe Thr Phe Thr Ile
210                 215                 220

Ser Ser Leu Gln Pro Glu Asp Ile Ala Thr Tyr Tyr Cys His Gln Tyr
225                 230                 235                 240

Leu Ser Ser Trp Thr Phe Gly Gln Gly Thr Lys Leu Glu Ile Lys Ala
                245                 250                 255

Ala Ala Leu Glu Ser Arg Gln Asp Asn Ser Arg Tyr Thr His Phe Leu
            260                 265                 270

Thr Gln His Tyr Asp Ala Lys Pro Gln Gly Arg Asp Asp Arg Tyr Cys
        275                 280                 285

Glu Ser Ile Met Arg Arg Arg Gly Leu Thr Ser Pro Cys Lys Asp Ile
    290                 295                 300

Asn Thr Phe Ile His Gly Asn Lys Arg Ser Ile Lys Ala Ile Cys Glu
305                 310                 315                 320
```

```
Asn Lys Asn Gly Asn Pro His Arg Glu Asn Leu Arg Ile Ser Lys Ser
                325                 330                 335

Ser Phe Gln Val Thr Thr Cys Lys Leu His Arg Arg Ser Pro Trp Pro
            340                 345                 350

Pro Cys Gln Tyr Arg Ala Thr Ala Gly Phe Arg Asn Val Val Val Ala
        355                 360                 365

Cys Glu Asn Gly Leu Pro Val His Leu Asp Gly Ser Ile Phe Arg Arg
    370                 375                 380

Pro Ala Glu His Glu Phe Arg Gly Gly Pro Glu Gln Lys Leu Ile Ser
385                 390                 395                 400

Glu Glu Asp Leu Asn Ser Ala Val Asp His His His His His His
                405                 410                 415

<210> SEQ ID NO 6
<211> LENGTH: 42
<212> TYPE: DNA
<213> ORGANISM: Artificial Sequence
<220> FEATURE:
<223> OTHER INFORMATION: Primer

<400> SEQUENCE: 6
ccacttgcaa gctacatcgg cgctcccect ggcctccatg cc                    42

<210> SEQ ID NO 7
<211> LENGTH: 42
<212> TYPE: DNA
<213> ORGANISM: Artificial Sequence
<220> FEATURE:
<223> OTHER INFORMATION: Primer

<400> SEQUENCE: 7
ggcatggagg ccaggggagag cgccgatgta gcttgcaagt gg                   42

<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8
cctgtccact tggatggatc aattttccgt cg                               32

<210> SEQ ID NO 9
<211> LENGTH: 32
<212> TYPE: DNA
<213> ORGANISM: Artificial Sequence
<220> FEATURE:
<223> OTHER INFORMATION: Primer

<400> SEQUENCE: 9
cgacggaaaa ttgatccatc caagtggaca gg                               32
```

HUMAN CYTOLYTIC FUSION PROTEINS

CROSS REFERENCE TO RELATED APPLICATIONS

This application is a US national phase application of international Application No. PCT/EP2015/063282, filed Jun. 15, 2015, which claims priority to European Application 14172288.4, filed Jun. 13, 2014, and to U.S. Provisional Patent Application No. 62/011,921, filed Jun. 13, 2014. The content of the preceding documents is herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with the file "10179-101294_sequencelisting_ST25" created on 12 Dec. 2016, filed on 13 Dec. 2016 and having a size of 17 Kilobytes. The sequence listing contained in this ASCII formatted document forms part of the specification and is herein incorporated by reference.

FIELD OF THE DISCLOSURE

The technology provided herein relates to novel human cytolytic fusion proteins (hCFPs) suitable to induce apoptosis in human cells comprising a target cell-specific binding component and a human effector domain, wherein the binding component comprises an antibody or an antibody fragment with an antigen-binding site for binding to the cellular surface receptor CD64 and the effector domain comprises a variant of wild type human angiogenin (Ang) or a functional fragment thereof; to nucleic acid molecules encoding said recombinant hCFPs, vectors and host cells containing said nucleic acids and methods for preparation and producing these hCFPs.

BACKGROUND

Immunotoxins (ITs) are recombinant fusion proteins originally developed for the treatment of malignant diseases. They comprise a toxic effector domain fused to a tumor cell-specific binding component, which is usually an antibody or a derivative thereof. Initially the antibody components were derived from mice and the toxins were derived from bacteria or plants, e.g. *Pseudomonas aeruginosa* exotoxin A (ETA), diphtheria toxin (DT) or ricin A. The major advantage of ITs compared to traditional chemotherapy is their exceptional target cell specificity, but their disadvantages include side effects caused by potential immunogenicity. Furthermore, the development of neutralizing antibodies against the toxins or murine parts of binding moieties limits the impact of long-term treatment due to accelerated clearance from the circulation. Highly toxic drugs and heterologous toxins conjugated to antibodies have been extensively tested, but for example the ADC gemtuzumab ozogamicin (Mylotarg®), approved by the US Food and Drug Administration for treatment of CD33+ acute myeloid leukemia was voluntarily withdrawn from the market because of increased occurrence of fatalities caused by hepato-occlusive disease upon treatment.

In order to circumvent the side effects caused by potential immunogenicity, the murine antibody components have been replaced by humanized or fully human counterparts and the bacterial and plant toxins have been replaced by human pro-apoptotic enzymes such as granzymes or ribonucleases (RNases). Granzyme B activates the caspase cascade whereas the RNase angiogenin (Ang) cleaves tRNA, both events leading to the induction of apoptosis. Fusion proteins that consist of a disease-specific binding component (e.g. scFvs, cytokines or peptide ligands) fused to a human pro-apoptotic enzyme are known as 'human cytolytic fusion proteins' (hCFPs) and have already proven their potential in several applications (Stahnke, B., et al., Mol Cancer Ther, 2008. 7(9): p. 2924-32; Huhn, M., et al., Cancer Res, 2001. 61(24): p. 8737-42; Krauss, J., et al., Br J Haematol, 2005. 128(5): p. 602-9; Schiffer, S., et al., Antibodies, 2013. 2(1): p. 9-18).

Nevertheless, the improvement of hCFPs is necessary because their cytotoxic efficacy is much lower than that of conventional ITs. Consequently, higher doses are needed to achieve the same therapeutic effect and the risk of inducing a treatment-associated immune response is therefore greater. The lower efficacy of hCFPs may also reflect the absence of natural translocation domains in human pro-apoptotic proteins. These are present in bacterial and plant toxins and promote endosomal release, so that the cytotoxic enzymes are delivered into the cytosol. Artificial adapter peptides have recently been designed to promote the release of hCFPs from endosomes and by this increase their cytotoxic efficacy.

The generation of RNase angiogenin (Ang)-based hCFPs and the cell-specific elimination of pathogenic cell populations worked successful in several studies so far. Nevertheless, the $IC_{50}$ of angiogenin-based hCFPs is significantly higher on different cell lines than for ITs containing ETA, diphtheria toxin or ricin, which are generally in the picomolar range (Ribbert, T., et al., Br J Dermatol, 2010. 163(2): p. 279-86; Zhong, R. K., et al., J Hematother Stem Cell Res, 2001. 10(1): p. 95-105). The greatest limitation affecting the inhibition of protein biosynthesis by angiogenin is the presence of its natural inhibitor RNH1 (also known as RI, RNH or PRI). This protein has a horseshoe-shaped structure that binds all monomeric members of the pancreatic RNase family with extraordinary affinity (De Lorenzo, C., et al., FEBS Lett, 2007. 581(2): p. 296-300). It is one of the strongest protein interactions discovered thus far, with a $Ki \approx 10^{-13}$-$10^{-16}$ for angiogenin, which helps to protect cellular nucleic acids against invading secretory RNases. The RNase-inhibitor complex has a half-life of more than 24 h, which corresponds with the low Ki value and completely inhibits the ribonucleolytic and angiogenic activity of Ang. RNH1 is continuously expressed in all human cell types and its abundance is $\geq 0.01\%$ of the total intracellular protein content. It is predominantly located in the cytosol but is also found in mitochondria and the nucleus where it is thought to participate in the oxidative stress response. The cytotoxic activity of hCFPs based on RNases is therefore dependent on the delivery of sufficient amounts of RNase to overcome inhibition by RNH1 in the cytosol.

An additional limitation of angiogenin as a human CFP effector domain is its weak enzymatic activity towards standard RNase substrates compared to other members of the pancreatic RNase superfamily (Russo, N., et al., Proc Natl Acad Sci USA, 1994. 91(8): p. 2920-4).

Furthermore, human pancreatic RNase nor RI evasive variants thereof proved to be suitable as effector components for a therapeutic IgG antibody platform. Further, there are also doubts about whether the effector mechanism of "cytotoxic" RNases is only dependent on their ribonucleolytic activity because there is no correlation between catalytic efficiency of different RNases and their cytotoxic properties, suggesting more complex mechanisms than unspecific RNA cleavage (Schirrmann, T., et al., MAbs, 2014. 6(2): p. 367-80). Rather, the cytosolic delivery of ribonucleases, which is among dependent on the used scFv and the intracellular routing taking place after CFP-antigen complex internalization, seems to be crucial. Thus the chosen scFv, in combination with the ribonuclease, has to accomplish several requirements to acquire CFP cytotoxicity that also includes the shunning of endosome fusion with intracellular lysosomal compartments if no translocation domains are explicitly available.

Therefore, the availability of novel and improved human cytolytic fusion proteins (hCFPs) would be highly advantageous.

SUMMARY OF THE DISCLOSURE

In a first aspect, the present disclosure pertains to selected and highly specific human cytolytic fusion proteins (hCFPs) comprising an effective angiogenin variant or functional fragment thereof as a human effector domain that induces apoptosis in combination with a specific and suitable target cell-specific binding domain.

Therefore, embodiments of the disclosure provides recombinant human cytolytic fusion proteins (hCFPs) suitable to induce apoptosis in human cells comprising a target cell-specific binding component and a human effector domain, wherein the binding component comprises an antibody or an antibody fragment with an antigen-binding site for binding to the cellular surface receptor CD64, and the effector domain comprises a variant or a functional fragment of wild type human angiogenin (Ang) as shown in SEQ ID NO: 1.

In still another aspect, embodiments of this disclosure provide nucleic acids encoding hCFPs as disclosed herein, as well as vectors and host cells comprising such nucleic acids.

In other aspects, this disclosure relates to compositions comprising hCFPs as described herein, wherein the hCFPs may be useful for, or used in, therapeutical, cosmetic and/or diagnostic applications. In one advantageous embodiment, the composition is used as a therapeutical composition for the treatment of cancer.

In still another aspect, embodiments of this disclosure provide medicaments comprising a recombinant human cytolytic fusion protein (hCFP) according to the present disclosure in combinations with a pharmacologically acceptable carrier.

In a further aspect, embodiments of this disclosure relate to methods for producing the hCFPs in a host cell by transforming the host cell with a DNA construct, advantageously including a promoter having transcriptional activity in the host cell, cultivating the transformed host cell in a suitable culture medium to allow expression of said hCFPs and producing the hCFPs. The method may also include isolating/purifying the produced hCFPs.

A further aspect pertains to methods of treating a malignant disease, an allergy, autoimmune reaction, tissue rejection reaction, or chronic inflammation reaction comprising administering an effective amount of the recombinant human cytolytic fusion protein (hCFP) according to the present disclosure to a patient in need thereof.

Before the disclosure is described in detail, it is to be understood that this disclosure is not limited to the particular hCFPs and production methods described in the present disclosure. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

BRIEF DESCRIPTION OF THE DRAWINGS

FIG. 1 is a diagram showing the binding activities of 1 μg hCFPs on $CD64^+$ HL-60 cells (A), human activated Mϕ (B) and $CD64^-$ L-540cy cells as negative control (C). The cells were incubated for 15 min with the fusion proteins and 10 min with the detection antibody on ice. After each incubation step, the cells were washed twice in PBS. Key: gray dots, cells stained with anti-$His_5$ Alexa Fluor 488; solid gray, cells incubated with wild-type H22-Ang; gray dashes, cells incubated with H22-Ang $GGRR_{mut}$; solid black, cells incubated with H22-Ang $GGRR/QG_{mut}$; black dashes, cells incubated with H22-Ang $QG_{mut}$.

FIG. 2(A) is an agarose gel picture, wherein 600 ng yeast tRNA was incubated with several concentrations of the hCFPs for 90 min at 37° C. 100 ng RNase A was used as a positive control whereas RNase-free water was added to the negative control sample. To visualize the dose-dependent degradation process, the samples were separated by 1% agarose gel electrophoresis and fragment bands were detected under UV light. Lanes: +=positive control, −=negative control, 1=1.5 μg hCFP, 2=1.0 μg, 3=0.5 μg, 4=0.25 μg. FIG. 2(B) is a diagram that represents the remaining tRNA band intensities in relation to the applied hCFP amounts. FIG. 2(C) shows an agarose gel picture, wherein 600 ng yeast tRNA was incubated with 1 μg hCFPs and 40 U RNH1 (corresponding to 0.6±0.05 μg) to inhibit the degradation as a function of the binding affinity. The other reaction conditions were unchanged. Lanes: +=positive control, −=negative control, 1=no inhibitor added, 2=40 U RNH1 added. FIG. 2(D) is a diagram that shows the remaining tRNA band intensities after 90 min incubation with hCFP/RNH1. Statistical analysis was carried out using GraphPad Prism software v5. Data were expressed as the mean±standard deviation (SD) as indicated. Statistical comparisons were made using a two-tailed unpaired Student's t test. $*p \leq 0.05$, $p \leq 0.01$, $*p \leq 0.001$.

FIG. 3 is a diagram presenting the time-dependent substrate conversion by the different Ang variants fused to H22(scFv) as a function of ribonucleolytic activity. The substrate was RNA coupled to a fluorophore and quencher, which was incubated for 3 h at 37° C. with each H22-Ang variant. The intact substrate does not produce a fluorescent signal at 520 nm because of the proximity between quencher and fluorophore. However, when both components are separated by substrate cleavage, the rising signal is a function of the RNase activity of the hCFP. The data were fitted using GraphPad Prism software v5.

FIG. 4 shows two diagrams, each representing the cytotoxic effect of the angiogenin variants fused to H22(scFv) on (A) IFNγ-stimulated $CD64^+$ HL-60 cells and (B) activated hMϕ. The cells were incubated with serial dilutions of each hCFP for 72 h at 37° C. under a 5% $CO_2$ atmosphere. Cell viability was then determined by XTT salt conversion after incubation for 4 h. The resulting $IC_{50}$ values against HL-60 cells were 10±2.7 nM (H22-Ang WT), 6.7±2.3 nM (H22-Ang $QG_{mut}$), 0.57±0.14 nM (H22-Ang $GGRR_{mut}$) and 4.2±1.8 nM (H22-Ang $GGRR/QG_{mut}$). The resulting $IC_{50}$ values against activated human Mϕ were 287±39 pM (H22-

Ang WT), 153±42 pM (H22-Ang QG$_{mut}$), 43±5.6 pM (H22-Ang GGRR$_{mut}$) and 75±2 pM (H22-Ang GGRR/QG$_{mut}$).

FIG. 5(A) is a western blot showing the inhibitor quantity found in the target cells. The cell lysates of HL-60 and activated Mφ were separated by SDS-PAGE and transferred onto a nitrocellulose membrane. RNH1 was specifically detected by ECL chemiluminescence imaging (white protein bands). The dark protein bands are β-actin, detected by subsequent conversion of a DAB peroxidase substrate. Equal loading was verified by the comparable amount of β-actin in each sample. Lanes: M: NEB pre-stained protein marker, 1: IFNγ-stimulated HL-60 cells, 2: activated hMφ. FIG. 5(B) shows the corresponding protein content, whereas band intensities were analyzed by 2D densitometry and the RNH1 content for each sample was normalized to 100 U of β-actin. Statistical analysis was carried out using GraphPad Prism software v5. Data were expressed as the mean±standard deviation (SD) as indicated. Statistical comparisons were made using a two-tailed unpaired Student's t test. *p≤0.05, p≤0.01, *p≤0.001

FIG. 6 shows the used amino acid sequence of human wild-type angiogenin without N-terminal signal peptide sequence (SEQ ID NO. 1.)

FIG. 7 shows amino acid sequences of embodiments of cytolytic fusion proteins (hCFPs) according to the present disclosure. H22-Ang WT (SEQ ID NO. 2), H22-Ang GGRR$_{mut}$ (SEQ ID NO. 3), H22-Ang QG$_{mut}$ (SEQ ID NO. 4) and H22-Ang GGRR/QG$_{mut}$ (SEQ ID NO. 5). Underlined=H22 (scFv), dotted=Ang WT or Ang-variant.

DETAILED DESCRIPTION OF THIS DISCLOSURE

The present disclosure provides novel recombinant human cytolytic fusion proteins (hCFPs) suitable to induce apoptosis in human CD64 expressing cells comprising a target cell-specific binding component and a human effector domain, wherein the binding component comprises an antibody or an antibody fragment with an antigen-binding site for binding to the cellular surface receptor CD64, and the effector domain comprises a variant or a functional fragment of wild type human angiogenin (Ang) as shown in SEQ ID NO: 1.

Advantageous embodiments of the present disclosure pertains to recombinant human cytolytic fusion proteins (hCFPs) suitable to induce apoptosis in human cells comprising a target cell-specific binding component and a human effector domain, wherein the binding component comprises an antibody or an antibody fragment with an antigen-binding site for binding to the cellular surface receptor CD64, and the effector domain comprises a variant or a functional fragment of wild type human angiogenin (Ang) as shown in SEQ ID NO: 1.

Figure 2:
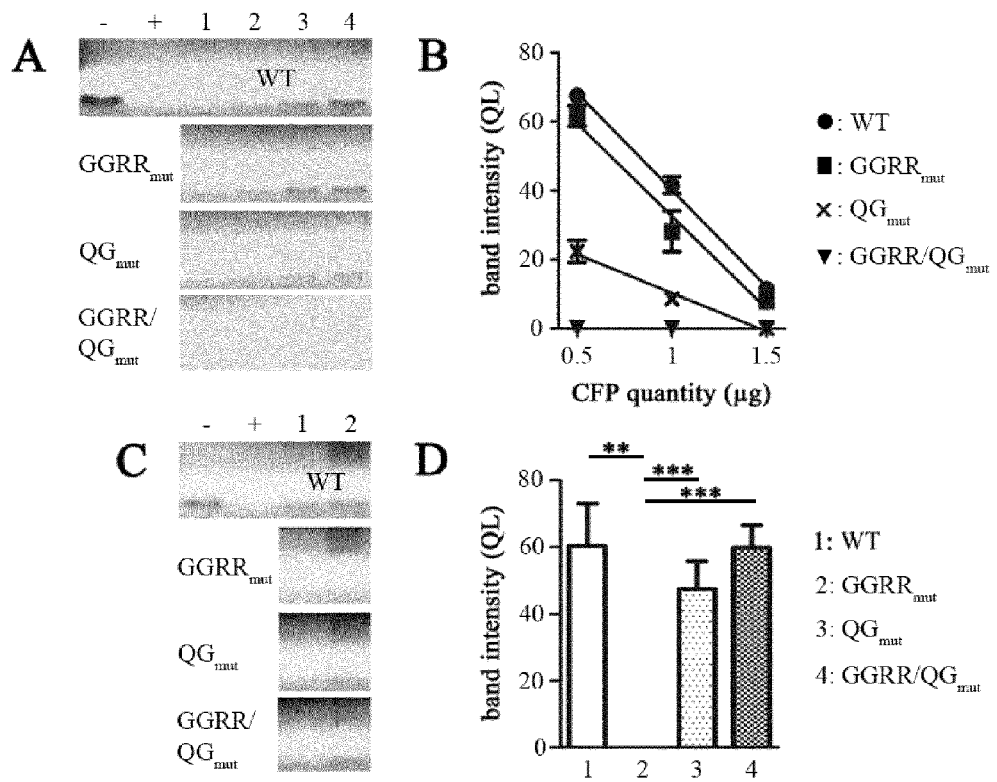
Figure 3:
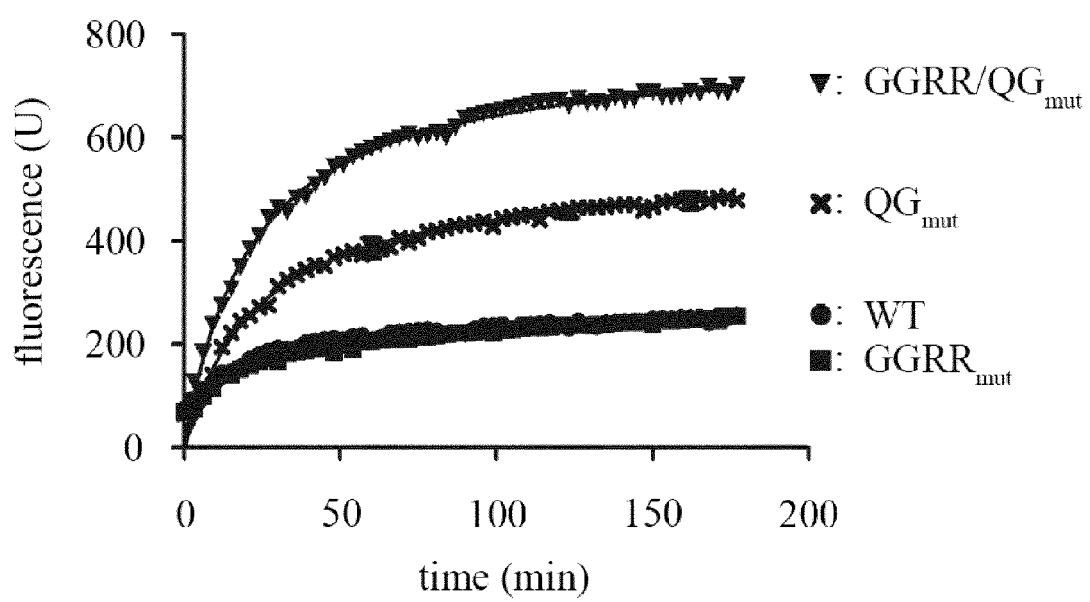

The in vitro enzymatic activity of the hCFPs according to the present disclosure were demonstrated by using a yeast tRNA substrate assay (FIGS. 2A and B). The results show that the wild-type enzyme and the G85R/G86R mutant have similar levels of RNase activity. The Ang variant Q117G is more enzymatically active because the active center accessibility for the substrate is improved by removing an obstructing residue. In contrast, the wild-type and G85R/G86R mutant versions must undergo a conformational rearrangement to uncover their active center and make it available for efficient substrate binding. Surprisingly, the combination of G85R/G86R and Q117G (Ang GGRR/QG$_{mut}$) demonstrated even greater RNase activity than Ang QG$_{mut}$. Therefore, the combination of amino acid exchanges have a synergistic impact on the three-dimensional enzyme structure, facilitating substrate binding, improving the accessibility of the active center and perhaps even increasing the enzymatic activity. The RNase activity of each Ang variant was confirmed by monitoring RNA degradation kinetics (FIG. 3). This procedure, based on the digestion with a coupled fluorophore and quencher allows the sensitive characterization of RNase activity. The novel angiogenin variant GGRR/QG$_{mut}$ achieves a substrate cleavage activity that is higher than for any other Ang mutants described in the prior art. The inhibition susceptibility for each Ang variant towards RNH1 was determined by the addition of the inhibitor to 1 µg CFP (FIG. 2C). The results show that the degradation efficiency of H22-Ang GGRR$_{mut}$ clearly reflects its lower sensitivity towards RNH1 (FIG. 2D). Surprisingly, H22-Ang GGRR/QG$_{mut}$ showed similar activity against yeast tRNA as the wild-type enzyme and the QG mutant. The low activity of GGRR/QG$_{mut}$ in the presence of the inhibitor, despite its high intrinsic activity, suggests that its sensitivity towards RNH1 is comparable to the wild-type enzyme. Therefore, a suitable binding surface for RNH1 can be restored by the combination of the GGRR and QG mutations in a single polypeptide domain.

Results presented here are documenting unpredictably high functional activity of anti-C64 binding ligand with the Ang mutant GGRR even outperforming the combination Ang GGRR/QG$_{mut}$. This exceptional functional activity of the GGRR mutant with other ligands binding to internalizing cell surface molecules has not been confirmed with single chain antibodies binding to e.g. epidermal growth factor receptor, CD30, CD33, or CD123 (data not shown).

The term "target cell-specific binding component" used herein comprises polypeptides having a binding activity for cellular surface structures. For example, the polypeptide based ligands may be provided with a cell targeting moiety that is a moiety that binds to and/or is internalized by only a selected population of cells such as cells expressing the cellular receptor CD64. Such a cell targeting may, for example, comprise an antibody, a growth factor, a hormone, a cytokine, an aptamer or an avimer that binds to a cell surface protein. Examples for binding moieties comprised in the ligand are affinity moieties from affinity substances or affinity substances in their entirety selected from the group consisting of antibodies, antibody fragments, receptor ligands, enzyme substrates, lectins, cytokines, lymphokines, interleukins, angiogenic or virulence factors, allergens, peptidic allergens, recombinant allergens, allergen-idiotypical antibodies, autoimmune-provoking structures, tissue-rejection-inducing structures, immunoglobulin constant regions and their derivatives, mutants or combinations thereof. In particular the target cell-specific binding component specifically binds to CD64.

In an advantageous embodiment, the target cell-specific binding component is an antibody or an antibody fragment selected from the group consisting of a monoclonal antibody, Fab, scFv; single domain, or a fragment thereof, bis scFv, Fab$_2$, Fab$_3$, minibody, diabody, triplebody, tetrabody and tandab.

In an advantageous embodiment, the target cell-specific binding component is a human antibody or human antibody fragment that specifically binds to CD64.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to V.sub.H-C.sub.H1 by a disulfide bond. The $F(ab)'_2$ may be reduced under mild conditions to break the disulfide linkage in the hinge region thereby converting the $(Fab')_2$ dimer into two Fab' monomers. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA technology. Thus, the term antibody, as used herein also includes antibody fragments either produced by the modification of whole antibodies or synthesized de novo using recombinant DNA technologies. Preferred antibodies include single chain antibodies (antibodies that exist as a single polypeptide chain), more preferably single chain Fv antibodies (scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston et al. (1988) Proc. Nat. Acad. Sci. USA, 85: 5879-5883. While the $V_H$ and $V_L$ are connected to each as a single polypeptide chain, the $V_H$ and $V_L$ domains associate non-covalently.

An "antigen-binding site" or "binding moiety" in an antibody or antibody fragment refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. Sequences of proteins of immunological interest, 4th ed. U.S. Dept. Health and Human Services, Public Health Services, Bethesda, Md. (1987).

For example, in advantageous embodiments of the present disclosure, the target cell-specific binding component that is capable to bind specifically to CD64 is an antibody. In general the term antibody includes, but is not limited to, polyclonal antibodies, monoclonal antibodies, single chain antibodies, humanized antibodies, minibodies, diabodies, triplebodies as well as antibody fragments, such as Fab', Fab, F(ab')2, single domain antibodies.

The phrase "specifically binds to CD64" refers to a binding reaction, which is determinative of the presence of the CD64 protein in the presence of a heterogeneous population of proteins and other biologics. Thus, under designated immunoassay conditions, the specified antibodies or antibody fragments bind to CD64 and do not bind in a significant amount to other proteins present in the sample. Specific binding to a protein under such conditions may require an antibody or antibody fragment that is selected for its specificity for CD64.

The terms "polypeptide", "peptide", or "protein" are used interchangeably herein to designate a linear series of amino acid residues connected one to the other by peptide bonds between the alpha-amino and carboxyl groups of adjacent residues. The amino acid residues are preferably in the natural "L" isomeric form. However, residues in the "D" isomeric form can be substituted for any L-amino acid residue, as long as the desired functional property is retained by the polypeptide. In addition, the amino acids, in addition to the 20 "standard" amino acids, include modified and unusual amino acids.

As used herein, the term "human antibodies" or "human antibody fragment" means that the framework regions of an immunoglobulin or an immunoglobulin fragment are derived from human immunoglobulin sequences.

As used herein, the term "single chain antibody fragments" (scFv) refers to antibodies prepared by determining the binding domains (both heavy and light chains) of a binding antibody, and supplying a linking moiety, which permits preservation of the binding function. This forms, in essence, a radically abbreviated antibody, having only that part of the variable domain necessary for binding to the antigen. Determination and construction of single chain antibodies are described in U.S. Pat. No. 4,946,778 by Ladner et al.

The "human effector domain", here also called "cell-killing domain" of the hCFP is a variant/mutant of human angiogenin. Angiogenin is a 14-kDa stress-activated enzyme also known as RNase 5, which acts as a potent stimulator of neovascularization and shares 33% sequence identity with pancreatic RNase A. Depending on cell density and stress factors, Ang undergoes rapid nuclear translocation due to the presence of an N-terminal nuclear localization signal. Under physiological conditions, angiogenin acts as a transcription factor for ribosomal RNA (rRNA) and thereby enhances the biosynthesis of components necessary for blood vessel growth as well as primary tumor development and metastasis. In contrast, the same molecule can inhibit cell-free protein synthesis by cleaving 5S, 18S and 28S rRNA as well as transfer RNA (tRNA). This degradation process leads to the inactivation of ribosomes and the production of tRNA-derived stress-induced RNAs (tiRNAs), which displace eIF4G/A from capped and uncapped messenger RNAs (mRNAs) as well as eIF4F from the m7G-cap, ultimately resulting in translational repression. The amino acid sequence of human wild-type angionin without the N-terminal leader sequence (amino acids 1-24) is shown in SEQ ID NO. 1.

In advantageous embodiments, the variant of the wild type human angiogenin as shown in SEQ ID NO: 1 contains at least a substitution at a position that corresponds structurally or by amino acid sequence homology to position 117, and wherein the substitution is Q117G.

In another advantageous embodiment, the variant of the wild type human angiogenin as shown in SEQ ID NO: 1 contains at least two further substitutions at positions that correspond structurally or by amino acid sequence homology to positions 85 and 86, and wherein the substitutions are G85R and G86R.

In particular, the recombinant human cytolytic fusion protein according to the present comprises a variant of the wild type human angiogenin as shown in SEQ ID NO: 1, wherein the variant contains at least substitutions at positions that correspond structurally or by amino acid sequence homology to positions 85, 86 and 117, and wherein the substitutions are G85R, G86R and Q117G.

Therefore, advantageous embodiments pertains to recombinant human cytolytic fusion proteins according to of the present disclosure, wherein the variant of the wild type human angiogenin having an amino acid sequence that varies from the amino acid sequence of the wild type human angiogenin (SEQ ID NO: 1), wherein the amino acid sequence of said variant comprises at least one variation as compared with SEQ ID NO: 1, wherein the variation is a substitution selected from the group consisting of G85R, G86R and Q117G, and wherein the amino acid sequence of said variant is at least 80% identical to the amino acid sequence of SEQ ID NO: 1. In a further advantageous embodiment, the variants of the wild type human angiogenin comprises the substitutions G85R, G86R and Q117G.

In further embodiments, the variants are at least 85%, at least 90%, at least 95%, at least 97%, at least 98% or at least 99% identical to the amino acid sequence of SEQ ID NO: 1.

The term "functional fragment of wild type human angiogenin" is to be construed as meaning any fragment of wild type human angiogenin having the desired function. In relation to modulation of enzymatic activity, a functional fragment is a fragment capable of modulating the enzymatic activity. The present disclosure comprises also functional fragments of the wild type human angiogenin, wherein the functional fragments comprises the same mutation as the angiogenin variants described herein and are able to cleave 5S, 18S and 28S rRNA as well as transfer RNA (tRNA). It is appreciated that the exact quantitative effect of the functional fragment may be different from the effect of the full-length molecule. In some instances, the functional fragment may indeed be more effective than the full-length molecule. Furthermore, the use of fragments instead of full-length molecules may be advantageous in view of the smaller size of the fragments.

As used herein, the term "CD64" refers to a human surface molecule as extensively reviewed above. For immunization purposes CD64 antigen may be prepared by any technique known in the art.

Antibodies to human CD64 are known in the art. The present invention also contemplates a new use of recombinant derivatives of such antibodies as detailed above.

Alternatively, anti-human CD64 monoclonal antibodies can be produced using CD64 antigen binding to an irrelevant Fc as immunogen, provided that there is available a screening assay which distinguishes antibodies directed against other antigens present in the immunogenic composition. Also cells or membrane fractions containing the molecule of interest bound to an irrelevant Fc as immunogens may be used in order to preserve the conformational constraints provided by a membrane environment. Immunizing animals with whole cells or fractions thereof usually yields a strong immune response, which generates antibodies to a large number of different molecules. This broad immune response precludes the use of the CD64$^+$-cells in combination with purified CD64 antigen both bound to an irrelevant Fc in subsequent screening for specific antibody production by hybridoma clones derived from the mouse spleen or lymphocytes.

As used herein, the expression "killing of CD64 expressing cells" is to be understood as implying an inhibition of protein synthesis or induction of apoptosis resulting in elimination or death of these cells; various molecular mechanisms may be employed; for example mechanisms that alter the function of a cell, those that alter the gene expression pattern of a cell or those that directly affect the viability of a cell may be used.

As used herein, the expression "CD64 expressing cells" refers to cells with CD64 as surface antigen. CD64 is mainly expressed on monocytes, macrophages and antigen presenting cells (APCs). Any type of cell expressing CD64 may be envisaged for treatment with the recombinant hCFP or compositions comprising the same of the present disclosure.

A "target cell" refers to a cell or cell-type for which an internalizing antibody, antibody fragment or binding (poly) peptide is sought. The target cell is typically characterized by the expression or overexpression of the target molecule CD64 that is characteristic e.g. for some tumor cells like cells from the leukemia cell line HL-60. Therefore, the recombinant hCFP according to the present disclosure may be used in different indications like the treatment of malignant diseases, allergies, chronic inflammatory diseases, such as acute myeloid leukemia, arthritis, COPD including emphysema, intrinsic and extrinsic asthma; cutaneous disease including atopic dermatitis, polymorphic light eruption, SLE; autoimmune diseases, including graft versus host, multiple sclerosis, macrophage activation syndrome, rheumatoid arthritis, juvenile arthritis; intestinal diseases including Crohn's disease and chronic bowel disease.

A fusion protein in general is a chimeric molecule in which the constituent molecules are all polypeptides and are attached (fused) to each other through terminal peptide bonds so that the chimeric molecule is a continuous single-chain polypeptide. The various constituents can be directly attached to each other or can be coupled through one or more peptide linkers. In general, a chimeric molecule is a molecule in which two or more molecules that exist separately in their native state are joined together to form a single molecule having the desired functionality of all of its constituent molecules. While the chimeric molecule may be prepared by covalently linking two molecules each synthesized separately, one of skill in the art will appreciate that where the chimeric molecule is a fusion protein, the chimera may be prepared de novo as a single "joined" molecule.

The fusion protein according to the present disclosure comprises a target cell-specific binding component capable to bind to an epitope of CD64.

In particular, the hCFP may be a "recombinant" polypeptide, which is defined either by its method of production or its structure. In reference to its method of production, e.g. a product made by a process, the process involved uses recombinant nucleic acid techniques. In reference to structure, recombinant polynucleotides or polypeptides contain sequences from different sources. In particular, it encompasses polypeptides made by generating a sequence comprising two or more fragments, which are not naturally contiguous or operably linked to each other. Thus, for example, products made by transforming cells with any unnaturally occurring vector are encompassed. The term may also be construed to mean fusion protein which has been generated by the synthesis of a DNA molecule encoding the fusion protein and which DNA molecule expresses a fusion protein, or an amino acid sequence specifying the fusion protein, wherein the DNA or amino acid sequence has been obtained using synthetic DNA or amino acid sequence technology which is available and well known in the art.

In an embodiment, the fusion protein according to the present disclosure is a recombinant and/or synthetic fusion protein.

Furthermore, the encoding nucleotide sequences may be synthesized in vitro without the need for initial template DNA samples e.g. by oligonucleotide synthesis from digital genetic sequences and subsequent annealing of the resultant fragments. Desired protein sequences can be "reverse translated" e.g. using appropriate software tools. Due to the degeneracy of the universal genetic code, synonymous codons within the open-reading frame (i.e. the recombinant protein coding region) can be exchanged in different ways, e.g. to remove cis-acting instability elements (e.g. AUUUA), to remove, introduce or modify the secondary and tertiary mRNA structures (e.g. pseudoknots, stem-loops), to avoid self-complementary regions that might trigger post-transcriptional gene silencing (PGTS), to change the overall AT:GC content, or to adjust the codon-usage to the expression host. Such changes can be designed manually or by using appropriate software tools or through a combination.

In some embodiments, the binding structure of the fusion protein is an antibody- or peptide binding domain for ligand binding. The binding structure may comprise an immunoglobulin-derived variable domain that comprises a complete antigen-binding site for an epitope on the target CD64 in a single polypeptide chain. In an advantageous embodiment, the binding structure of the fusion protein is a single domain antibody fragment. Examples of such antibodies or fragments thereof are antibodies that specifically recognize an epitope that is present on the kappa or lambda light chain of chimeric, humanized or fully human antibodies or antibody fragments. In this example the human antibody is the ligand. Human antibodies comprise two kappa light chains, which comprise the epitopes.

In advantageous embodiments, the human cytolytic fusion protein (hCFP) comprises an amino acid sequence of SEQ ID NO: 3. (GGRR mutant).

In further embodiments, the present disclosure pertains to hCFPs that are at least 85%, at least 90%, at least 95%, at least 97%, at least 98% or at least 99% identical to the amino acid sequence of SEQ ID NO: 2.

Further embodiments of the present disclosure pertain to isolated nucleic acid molecules encoding a hCFP according to the present disclosure.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule, as it exists in natural cells. However, an isolated nucleic acid molecule includes a nucleic acid molecule contained in cells that ordinarily express the ligand, for example the antibody where, for example, the nucleic acid molecule is in a chromosomal location different from that of natural cells.

To express a fusion protein according to the present disclosure in a recombinant expression system, a DNA encoding the fusion protein or parts thereof, may be inserted into an expression vector such that the gene is operably linked to transcriptional and translational control sequences. In this context, the term "operably linked" means that a protein gene is ligated into a vector such that transcriptional and translational control sequences within the vector serve their intended function of regulating the transcription and translation of the protein gene. The expression vector and expression control sequences are chosen to be compatible with the expression host cell used. The isolated protein domain sequences are typically inserted into the same expression vector. The protein genes are inserted into the expression vector by standard methods. Additionally, the recombinant expression vector can encode a signal peptide that facilitates co-translational translocation of the nascent polypeptide chain into the endoplasmic reticulum (ER). The folded polypeptide (recombinant fusion protein according to this disclosure) may be secreted from a host cell or may be retained within the host cell. Intracellular retention or targeting can be achieved by the use of an appropriate targeting peptide such as C-terminal KDEL-tag for ER retrieval.

In general, those skilled in the art are well able to construct vectors and design protocols for recombinant gene expression. For further details see, for example, Molecular Cloning: a Laboratory Manual: 2nd edition, Sambrook et al., 1989, Cold Spring Harbor Laboratory Press (or later editions of this work) and Current Protocols in Molecular Biology, Second Edition, Ausubel et al. eds., John Wiley & Sons, 1992, which are incorporated herein by reference.

Furthermore, the present disclosure relates to nucleic acid molecules or nucleic acids encoding such a fusion protein as well as to vectors comprising the nucleic acid molecule and host cells comprising a nucleic acid molecule encoding said fusion protein or a vector comprising said vector. The disclosure pertains also to methods of manufacturing said recombinant fusion proteins in a recombinant expression system.

The term "vector" includes a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g. bacterial vectors having a bacterial origin of replication and episomal mammalian vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression system" or "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g. replication-defective retroviruses, adenoviruses and adeno-associated viruses), which serve equivalent functions.

The present disclosure is also directed to a host cell with a vector comprising the recombinant fusion proteins according to the present disclosure. The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Host cells include progeny of a single host cell, and the progeny may not necessarily be completely identical (in morphology or in total DNA complement) to the original parent cell due to natural, accidental, or deliberate mutation and/or change. A host cell includes a cell transfected or infected in vivo or in vitro with a recombinant vector or a polynucleotide of the present disclosure. A host cell, which comprises a recombinant vector of the disclosure, may also be referred to as a "recombinant host cell".

The term "host cell(s)" refers to cell(s), which may be used in a process for purifying a recombinant protein in accordance with the present disclosure. Such host cells carry the protein of interest (POI). A host cell may also be referred to as a protein-expressing cell. A host cell, according to the present invention, may be, but is not limited to, prokaryotic cells, eukaryotic cells, archaebacteria, bacterial cells, insect cells, yeast, mammal cells, and/or plant cells. Bacteria envisioned as host cells can be either gram-negative or gram-positive, e.g. *Escherichia coli, Erwinia* sp., *Kiebsellia* sp., *Lactobacillus* sp. or *Bacillus subtilis*. Typical yeast host cells are selected from the group consisting of *Saccharomyces cerevisiae, Hansenula polymorpha* and *Pichia pastoris*. In some advantageous embodiments, the host cell is a HEK293T cell.

The recombinant human cytolytic fusion protein (hCFP) of the present disclosure can be used with a "pharmaceutically acceptable carrier" which includes any and all solvents, dispersion media, coatings, surfactants, antioxidants, preservatives (e.g. antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art.

A pharmaceutically acceptable carrier is preferably formulated for administration to a human, although in certain embodiments it may be desirable to use a pharmaceutically acceptable carrier that is formulated for administration to a non-human animal, such as a canine, but which would not be acceptable (e.g. due to governmental regulations) for administration to a human. Except insofar as any conventional carrier is incompatible with the active ingredient, its use in the therapeutic or pharmaceutical compositions is contemplated.

The actual dosage amount of a composition of the present disclosure administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In advantageous embodiments, recombinant human cytolytic fusion proteins according to the disclosure are used for treating a malignant disease, an allergy, autoimmune disease, tissue rejection reaction, or chronic inflammation reaction.

The following methods and examples are offered for illustrative purposes only, and are not intended to limit the scope of the present disclosure in any way.

METHODS AND EXAMPLES

It should be understood that the following examples are for illustrative purpose only and are not to be construed as limiting this disclosure in any manner. All publications, patents, and patent applications cited herein are hereby incorporated by reference in their entirety for all purposes.

1. Site-Directed Mutagenesis

The wild-type H22-Ang sequence was inserted into the expression vector pMS (Stocker, M., et al., Protein Expr Purif, 2003. 28(2): p. 211-9) and modified by site-directed mutagenesis using the QuikChange II XL Site-Directed Mutagenesis Kit (Agilent Technologies, Böblingen, Germany). The following exchange oligonucleotides were synthesized by Eurofins (Ebersberg, Germany) and used for mutagenesis PCR: $GGRR_{mut}$ for (5'-CCA CTT GCA AGC TAC ATC GGC GCT CCC CCT GGC CTC CAT GCC-3'), $GGRR_{mut}$ rev (5'-GGC ATG GAG GCC AGG GGG AGC GCC GAT GTA GCT TGC AAG TGG-3'), $QG_{mut}$ for (5'-CCT GTC CAC TTG GAT GGA TCA ATT TTC CGT CG-3') and $QG_{mut}$ rev (5'-CGA CGG AAA ATT GAT CCA TCC AAG TGG ACA GG-3'). The annealing temperature was 75° C. for the GGRR mutation and 57° C. for the QG exchange. The mutations were verified by DNA sequencing using an ABI Prism 3700 DNA Analyzer and BigDye cycle sequencing terminator chemistry (Applied Biosystems, Carlsbad, USA).

2. Cell Culture and hCFP Expression

HL-60 (ATCC, CCL-240) and L-540cy cells (kindly provided by Prof. Dr. med. Andreas Engert, University Hospital Cologne, Germany) were cultured under standard conditions (RPMI 1640 medium, 10% fetal calf serum, 37° C., 5% $CO_2$) without selection (Gallagher, R., et al., Blood, 1979. 54(3): p. 713-33; Diehl, v., et al., Cancer Res Clin Oncol, 1981. 101(1): p. 111-24). other cells were cultivated as previously described (Dmitrij Hristodorov, CD64-mediated specific elimination of M1-polarized macrophages: implications for therapeutic intervention in chronic inflammatory diseases, doctoral thesis, 2013, RWTH Aachen, at web site: darwin.bth.rwth-aachen.de/opus/volltexte/2013/4705/). The pMS expression vectors were used for the transfection of HEK293T cells (ATCC, Wesel, Germany, CRL-11268) using ROTI-FECT (Carl Roth, Karlsruhe, Germany) according to the manufacturer's instructions. Briefly, 2 μg of DNA was mixed with 10 μl of ROTI-FECT and applied to the cells for 4 h. For selection, the cultures were then supplemented with 100 ng/ml ZEOCIN (Invitrogen, Carlsbad, USA).

3. Purification of hCFPs

The recombinant hCFPs were purified from the cell culture supernatant by IMAC using a 5-ml $Ni^{2+}$-NTA Superflow cartridge (Qiagen, Hilden, Germany) on a ÄKTA purifier system (Amersham Pharmacia Biotech, Freiburg, Germany). Elution fractions were pooled and concentrated using Vivaspin 6 columns (Sartorius, Goettingen, Germany). After overnight dialysis against 1×PBS at 4° C., the hCFPs were passed through a 0.22 μm sterile filter (Nalgene, Roskilde, Denmark). Protein concentration was estimated by SDS-PAGE and staining with Coomassie Brilliant Blue followed by image analysis using AIDA biopackage software (Raytest GmbH, Straubenhardt, Germany) against 0.25-3 µg standards of bovine serum albumin (BSA).

Successful site-directed mutagenesis of the wild-type angiogenin DNA sequence was verified by sequencing. The corresponding expression vectors were successfully introduced into HEK293T cells as shown by eGFP reporter gene expression and the survival of transfected cells under selection pressure. The expression of the hCFPs and their secretion into the cell culture supernatant was confirmed by flow cytometry analysis of hIFNγ-stimulated HL-60 cells (data not shown). The protein purity was estimated to be 60-90% based on gel staining with Coomassie Brilliant Blue and AIDA analysis of band intensities. Calculated expression yields were between 360 µg and 2.3 mg per liter cell culture supernatant (Table 1).

TABLE 1

Expression yields of H22-Ang variants

| hCFP | yield/l |
|---|---|
| H22-Ang WT | 1.9 mg |
| H22-Ang GGRR$_{mut}$ | 360 µg |
| H22-Ang QG$_{mut}$ | 2.3 mg |
| H22-Ang GGRR/QG$_{mut}$ | 1.7 mg |

4. Flow Cytometry

The binding of hCFPs to $6\times10^5$ CD64$^+$ HL-60 cells (stimulated with 300 U/ml IFNγ 24 h earlier) was evaluated by flow cytometry using the BD FACSVerse flow cytometer (Becton Dickinson, Heidelberg, Germany) and BD FACSuite analysis software. Briefly, the cells were incubated with 1 µg of purified hCFP for 15 min and 1 µg/ml anti-His5 Alexa Fluor 488 antibody (Qiagen, Hilden, Germany) for 10 min, in each case on ice with intermediate washes in 1.8 ml 1×PBS. L-540cy cells were used as a negative control. Human Mφ were cultivated and activated as described below.

Specific and even binding activity was verified by flow cytometry after applying 1 µg of each hCFP onto hIFNγ-stimulated HL-60 cells and activated hMφ (FIG. 1). Nonspecific binding was ruled out because there was no fluorescence shift when L-540cy cells were exposed to the hCFPs as a negative control.

5. Isolation and Activation of hMφ from Buffy Coat-Derived PBMCs

Buffy coats were obtained from the Department of Transfusion Medicine, University Hospital RWTH Aachen, Germany. PBMCs were isolated and Mφ were activated as previously described (Schiffer, S., et al., Antibodies, 2013. 2(1): p. 9-18). Cell detachment was carried out by adding 1 ml accutase (PAA Laboratories, Pachingen, Austria) per T175 flask and incubating at 37° C. until no adherent cells remained.

6. In Vitro RNase and Inhibition Assays

The RNase activity of the fusion proteins was evaluated by in vitro tRNA degradation. Briefly, different amounts of each hCFP (0.25-1.5 µg) were incubated with 600 ng yeast tRNA (Sigma, Steinheim, Germany) in 20 µl buffer (RNase-free 30 mM Tris/NaCl pH 7.5) for 1.5 h using RNAse-free equipment. 1×TAE buffer was prepared with water treated with 1% DEPC (Carl Roth) and was used to prepare 1% agarose gels containing 0.1 µg/ml ethidium bromide and as the running buffer. A 5× loading buffer was prepared as previously described (Huhn, M., et al., Cancer Res, 2001. 61(24): p. 8737-42). Buffer containing 100 ng RNase A (Thermo Scientific, Schwerte, Germany) was used as a positive control and the same volume of DEPC-treated water was used as a negative control. Electrophoresis was carried out at 100 V for 10 min and bands were visualized by UV illumination. Inhibition susceptibility was demonstrated by adding 40 U commercial RNH1 (corresponding to 0.6±0.05 µg) to 1 µg CFP while the reaction conditions were maintained. Statistical analysis was carried out using GraphPad Prism software v5 (GraphPad Software Inc., La Jolla, Calif., USA). Data were expressed as the mean±standard deviation (SD) as indicated. Statistical comparisons were made using a two-tailed unpaired Student's t test. *p≤0.05, p≤0.01, *p≤0.001.

The RNase activity of each hCFP was tested in vitro by incubating different amounts of each fusion protein (0.25-1.5 µg) with 600 ng yeast tRNA at 37° C. for 1.5 h. To investigate the susceptibility of each variant to inhibition, 40 U of commercial RNH1 inhibitor was mixed with 1 µg CFP and the RNase activity was tested as described above. Based on the cleavage assay, the other reaction conditions were not changed, and this demonstrated that the tRNA cleavage activity was a function of inhibitor affinity (FIG. 2).

The variants QG$_{mut}$ and GGRR/QG$_{mut}$ showed more potent cleavage activity than the wild-type version when presented with yeast tRNA as a substrate. Including standard deviations, GGRR$_{mut}$ and wild-type Ang exhibited no significant difference in substrate conversion. However, in the presence of RNH1, the GGRR mutant showed the strongest cleavage activity and comparably low efficiencies were observed for all the other variants.

7. Determination of Substrate Cleavage Kinetics

We incubated 5 pM RNaseAlert substrate (Integrated DNA Technologies, Leuven, Belgium) with 10 pM hCFPs for 180 min at 37° C. in RNase-free 30 mM Tris/NaCl (pH 7.5) in a total reaction volume of 100 µl. The experiments were carried out in triplicate and 10 pM H22(scFv) was used instead of the hCFPs as a negative control. Samples containing 10 fM RNase A were used as a positive control. Fluorescence was measured using the "Tecan Genios Pro" microplate reader and Magellan 7.1 SP1 software, with an excitation wavelength of 485 nm and an emission wavelength of 520 nm. Measurements were taken four times per well at 3 min intervals. Between each cycle, the plate was stirred for 20 s in orbital mode with 5 mm amplitude. Final data evaluation was carried out using GraphPad Prism software v5.

Cleavage kinetics was analyzed for each hCFP using an RNA substrate with a coupled fluorophore and quencher. Separation of the fluorophores during substrate cleavage prevents further quenching and allows the detection of fluorescence at 520 nm (FIG. 3). Negative and positive controls were used to establish the expected fluorescence signals corresponding to full quenching and no quenching (data not shown). While wild-type Ang and the GGRR variant revealed a rather moderate substrate conversion, an increase in enzymatic activity could be detected using the QG variant. The highest fluorescence over time could be observed for GGRR/QG$_{mut}$ which directly correlates with its strong substrate conversion. These results can be aligned with the observations made using the yeast tRNA cleavage assay.

8. XTT Proliferation Assay

XTT assays were carried out as previously described (Schiffer, S., et al., Antibodies, 2013. 2(1): p. 9-18). Prior to each assay, HL-60 cells were seeded at a density of $1\times10^5$ cells/ml and stimulated with 300 U/ml hIFNγ for 24 h to upregulate the expression of CD64 (Bovolenta, C., et al., J Immunol, 1998. 160(2): p. 911-9). We also carried out XTT assays using 5×10⁵ human Mϕ per ml as described above. Raw data were fitted using GraphPad Prism software v5.

Figure 4:
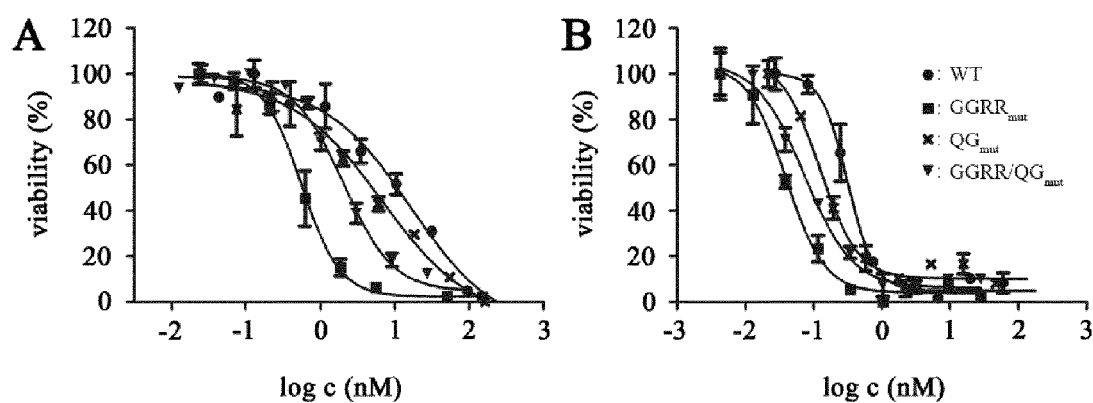

Viability assays were carried out to determine the specific in vitro cytotoxicity of the H22-Ang variants when incubated with hIFNγ-stimulated HL-60 and human Mϕ (FIG. 4). Each hCFP was also tested against CD64⁻ L-540cy cells as a negative control to rule out nonspecific cytotoxicity.

The wild-type fusion protein yielded an $IC_{50}$ value of 10±2.7 nM against hIFNγ-stimulated HL-60 cells, but the Q117G exchange improved the $IC_{50}$ value to 6.7±2.3 nM. However, an even greater increase in cytotoxicity was achieved by the G85R/G86R exchange, with the $IC_{50}$ value falling to 0.57±0.14 nM for H22-Ang $GGRR_{mut}$. The combination of both sets of exchanges in Ang $GGRR/QG_{mut}$ yielded an $IC_{50}$ value of 4.3±1.7 nM. When the fusion proteins were incubated with activated human Mϕ, the average $IC_{50}$ values were significantly lower: 287±39 pM for H22-Ang WT, 153±42 pM for the QG variant, 43±5.6 pM for $GGRR_{mut}$ and 75±2 pM for the combined mutant. None of the hCFPs demonstrated a cytotoxic effect against L-540cy cells (data not shown).

9. Apoptosis Assays

We suspended $5\times10^4$ hIFNγ-stimulated HL-60 cells per ml (300 U/ml) in R10 medium and seeded them into 24-well plates. After 24 h, 100 nM H22-Ang $GGRR_{mut}$ was applied in an end volume of 500 μl per well and the cells were incubated for a further 72 h at 37° C. and 5% $CO_2$. Negative control cells were treated with 30 μl PBS (100% viability) whereas positive control cells were treated with 30 μl Zeocin (0% viability). The cells were scraped and washed with 1× annexin V binding buffer containing 10 mM HEPES, 140 mM NaCl and 2.5 mM $CaCl_2$ (pH 7.4) followed by centrifugation (1500 rpm, 7 min, 4° C.). The pellet was resuspended in 450 μl R10 medium containing the annexin V-eGFP fusion protein and 50 μl of 10× annexin V binding buffer (Stöcker, M., et al., Protein Expr Purif, 2008. 58(2): p. 325-331). After incubating for 10 min in the dark and a washing step, the cells were resuspended in 1× annexin V binding buffer supplemented with 1 μg/ml propidium iodide. The induction of apoptosis was evaluated by flow cytometry on the FL-1 and FL-3 channels, counting $10^4$ cells (Verhoven, B., et al., J Exp Med, 1995. 182(5): p. 1597-601). L-540cy cells (Kapp, U., et al., Ann Oncol, 1994. 5 Suppl 1: p. 121-6) were used as negative control cell line and treated as described above.

Apoptotic cells were detected by annexin V/PI staining to gain further insight into the cytotoxic effect of Ang-based CFPs. We used H22-Ang $GGRR_{mut}$ as a representative fusion protein and incubated hIFNγ-stimulated HL-60 cells with 100 nM of the protein for 72 h, using L-540cy cells as negative control under the same conditions. The incubation of cells with recombinant annexin V-eGFP allowed the label to bind phosphatidylserine molecules on the surface of early apoptotic cells. Late apoptotic cells were visualized by simultaneous propidium iodide staining. Data were acquired by flow cytometry, plotting fluorescence channel FL-1 against FL-3 (Table 2). The proportions of early apoptotic, late apoptotic and necrotic cells were determined and differences between the cells treated with PBS and the hCFP were calculated. Exposure to the hCFP increased the proportion of early apoptotic HL-60 cells by 13.6%, and the proportion of late apoptotic HL-60 cells by 24.7%. There were no such increases in the L-540cy cells, and the number of necrotic cells was unchanged in both cell lines.

TABLE 2

Cytotoxic effect of H22-Ang $GGRR_{mut}$ on HL-60 and L-540cy cells

| cell line | early apoptotic | late apoptotic | necrotic |
|---|---|---|---|
| HL-60 | +13.6% | +24.7% | +0.2% |
| L-540cy | −0.7% | −0.7% | +0.7% |

10. RNH1 Expression Profiling by Real-Time PCR

RNA was isolated from cells using the NucleoSpin® RNA II Kit (Macherey & Nagel, Düren, Germany) and cDNA was synthesized using the SuperScript™ III Cells-Direct cDNA Synthesis System Kit (Invitrogen, Carlsbad, USA) according to the manufacturer's instructions. The Hs_RNH1_2_SG QuantiTect Primer Assay (Qiagen, Hilden, Germany) was obtained from Source BioScience (Cambridge, UK, I.M.A.G.E) and a full-length cDNA clone IRAUp969G0610D was used as a positive control. Glyceraldehyde 3-phosphate dehydrogenase (GAPDH) was amplified for normalization using the primers GAPDH_for (5'-GGT ATC GTG GAA GGA CTC ATG AC-3') and GAPDH_rev (5'-ATG CCA GTG AGC TTC CCG TTC AG-3') kindly provided by PharmedArtis GmbH (Aachen, Germany). The QuantiFast SYBR Green PCR Kit (Qiagen, Hilden, Germany) was used according to the manufacturer's instructions on an Applied Biosystems® 7500 Real-Time PCR System (Life Technologies, Darmstadt, Germany) with the following settings: 10 min for the first denaturation at 95° C., 40 cycles of 15 s denaturation at 95° C. and annealing/elongation for 1 min at 60° C., melting curve analysis with 1 min at 20° C. followed by 1 min at 60° C. with a 100% slope and 1 min at 95° C. with a 0.5% slope. Relative quantification was achieved using the $NA/NB=2^{-\Delta CT}$ equation.

HL-60 cells and activated human Mϕ were used for the extraction of total RNA, and the RNH1 and GAPDH mRNAs were amplified using gene-specific primers. SYBR Green was added as a detection reagent to monitor the amplification process and to allow the quantitative comparison of RNH1 mRNA levels in the different cells, using GAPDH as a housekeeping gene for normalization. Melting curve analysis was carried out afterwards to verify specific fragment amplification. The observed CT values for GAPDH and RNH1 were used for relative quantification (Table 3). In HL-60 cells, the level of RNH1 gene expression was 22.5% relative to GAPDH but this fell to 11.9% in activated hMϕ. Melting curve analysis carried out after 40 amplification cycles confirmed the absence of nonspecific fragments in the tested samples (data not shown).

TABLE 3

RNH1 expression profiling in HL-60 cells and activated hMΦ

| cells | RNH1 % to GAPDH |
|---|---|
| HL-60 | 22.5% |
| hMΦ | 11.9% |

11. Detection of RNH1 in Target Cell Lysates

We lysed $8\times10^6$ cells for 1 h in 1×PBS buffer containing 1% Triton X-100 and protease inhibitor (Pierce Protease Inhibitor Tablet, Thermo Scientific, St. Leon-Rot, Germany) followed by sonication on ice (Bandelin Sonoplus MS72 sonotrode, three 15-s cycles at 50 W with 15-s cooling breaks). The cell debris was removed by centrifugation (16,000 g, 4° C., 10 min) and the protein content was determined by absorbance at 280 nm. Equal amounts of protein were then separated by SDS-PAGE on 12% polyacrylamide gels for 60 min at 160 V. The proteins were blotted onto nitrocellulose membrane (Carl Roth) (280 mA, 70 min, 4° C.) which was then blocked using Roti®-Block solution (Carl Roth) for 1 h at room temperature. The membrane was then incubated with mouse anti-RNH1 antibody F-5 (Santa Cruz Biotechnology, Heidelberg, Germany) and the signal was detected with a goat-anti-mouse antibody labeled with peroxidase (Sigma Aldrich, Steinheim, Germany), each for 60 min with intermediate washes in PBS supplemented with 0.05% Tween-20. Pierce ECL Western Blotting Substrate (Thermo Scientific, St. Leon-Rot, Germany) was added according to the manufacturer's instructions and protein bands were visualized using a Stella Reader (Raytest GmbH). Subsequent washing was carried out stringently using 1×PBS supplemented with 0.05% Tween-20. To verify equal loading, peroxidase-labeled mouse-anti-β-actin (Sigma Aldrich, Steinheim, Germany) was added to the membrane for 30 min and detected with SIGMAFAST™ DAB peroxidase substrate (Sigma Aldrich, Steinheim, Germany) according to the manufacturer's instructions to additionally visualize β-actin at 42 kDa. Images were evaluated using Adobe Photoshop CS5.1 (Adobe Systems GmbH, München, Germany) to overlay the pictures, and by 2D densitometry (AIDA biopackage software, Raytest GmbH). Statistical analysis was carried out using GraphPad Prism software v5. Data were expressed as the mean±standard deviation (SD) as indicated. Statistical comparisons were made using a two-tailed unpaired Student's t test. *$p \leq 0.05$, $p \leq 0.01$, *$p \leq 0.001$.

Figure 5:
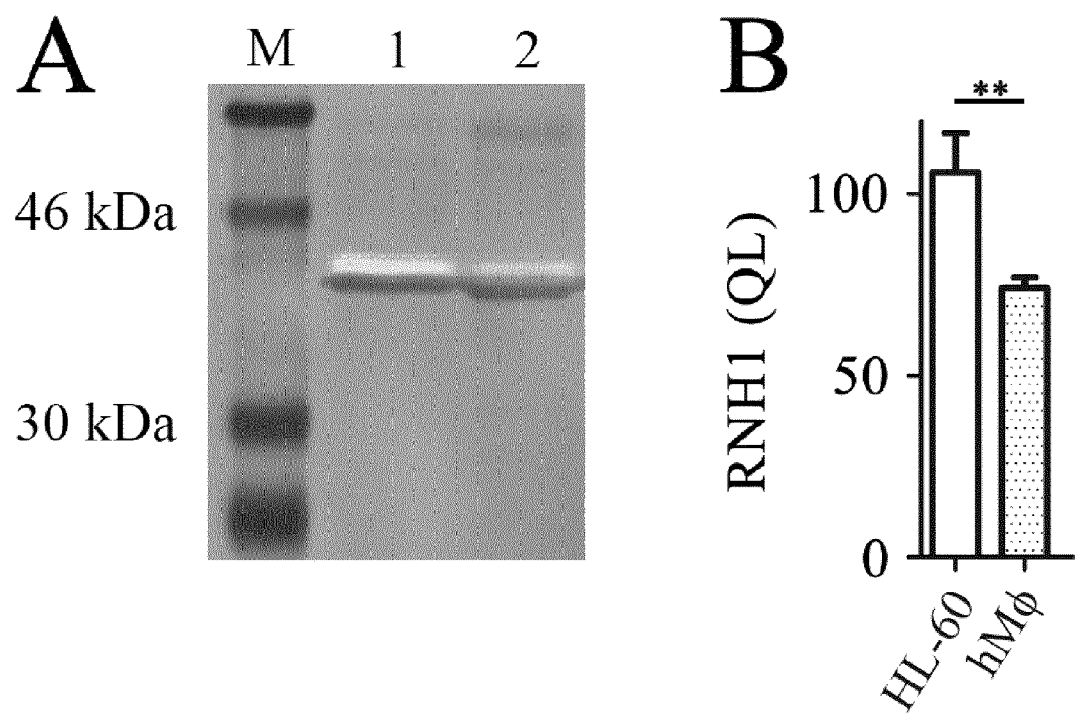

Stimulated HL-60 cells as well as activated hMφ were lysed and the lysates were fractionated by SDS-PAGE. The gels were blotted onto a nitrocellulose membrane and RNH1 was visualized specifically using an anti-RNH1 antibody followed by signal quantitation using a chemiluminescent detection. Equal loading in each gel lane was ensured by comparing the signal generated by the housekeeping protein β-actin (FIG. 5). Based on the yielded band pattern, a significant higher RNH1 quantity can be detected in the HL-60 cell lysate compared to that of activated hMφ.

What is claimed is:

1. A recombinant human cytolytic fusion protein (hCFP) suitable to induce apoptosis in human target cells, comprising a target cell-specific binding component and a human effector domain, wherein the binding component comprises an antibody or an antibody fragment with an antigen-binding site for binding to the cellular surface receptor CD64, and the effector domain comprises a variant or a functional fragment of wild type human angiogenin (Ang) as shown in SEQ ID NO: 1, wherein the variant of the wild type human angiogenin as shown in SEQ ID NO: 1 contains at least substitutions at positions that correspond structurally or by amino acid sequence homology to positions 85, 86 and 117, and wherein the substitutions are G85R, G86R and Q117G.

2. The recombinant human cytolytic fusion protein (hCFP) according to claim 1, wherein the antibody fragment is selected from the group consisting of a Fab, a scFv, a single domain, a bis scFv, a Fab$_2$, a Fab$_3$, a minibody, a diabody, a triplebody, a tetrabody, and a tandab.

3. The recombinant human cytolytic fusion protein (hCFP) according to claim 1, wherein the binding component is a CD64-specific single-chain variable fragment (scFv).

4. The recombinant human cytolytic fusion protein (hCFP) according to claim 1, wherein the binding component is the CD64-specific single-chain variable fragment H22(scFv).

5. A drug comprising the recombinant human cytolytic fusion protein (hCFP) according to claim 1 in combination with a pharmacologically acceptable carrier.

6. An isolated nucleic acid molecule encoding the recombinant human cytolytic fusion protein (hCFP) according to claim 1.

7. A vector comprising the nucleic acid molecule claim 6.

8. A host cell transformed with the vector of claim 7.

9. The host cell according to claim 8, wherein the host cell is a HEK293T cell.

10. A method for preparing a recombinant human cytolytic fusion protein (hCFP), the method comprising culturing the host cell of claim 8 and isolating the fusion protein from the cell culture.

11. A recombinant human cytolytic fusion protein (hCFP) suitable to induce apoptosis in human target cells, comprising a target cell-specific binding component and a human effector domain, wherein the binding component comprises an antibody or an antibody fragment with an antigen-binding site for binding to the cellular surface receptor CD64, and the effector domain comprises a variant or a functional fragment of wild type human angiogenin (Ang) as shown in SEQ ID NO: 1, wherein the amino acid sequence of the variant comprises at least one variation as compared with SEQ ID NO: 1, wherein the variant of the wild type human angiogenin comprises the substitutions G85R, G86R and Q117G, and wherein the amino acid sequence of the variant has a sequence identify of at least 80% to SEQ ID NO: 1.

12. An isolated nucleic acid molecule encoding the recombinant human cytolytic fusion protein (hCFP) according to claim 11.

13. A vector comprising a nucleic acid molecule encoding the recombinant human cytolytic fusion protein (hCFP) according to claim 11.

14. A recombinant human cytolytic fusion protein (hCFP) suitable to induce apoptosis in human target cells, comprising a target cell-specific binding component and a human effector domain, wherein the binding component comprises an antibody or an antibody fragment with an antigen-binding site for binding to the cellular surface receptor CD64, and the effector domain comprises a variant or a functional fragment of wild type human angiogenin (Ang) as shown in SEQ ID NO: 1, wherein the human cytolytic fusion protein (hCFP) comprises an amino acid sequence of SEQ ID NO: 3 or SEQ ID NO: 5.

15. An isolated nucleic acid molecule encoding the recombinant human cytolytic fusion protein (hCFP) according to claim 14.

16. A vector comprising a nucleic acid molecule encoding the recombinant human cytolytic fusion protein (hCFP) according to claim 14.

17. A method of treating a malignant disease, the method comprising administering an effective amount of the recombinant human cytolytic fusion protein (hCFP) according to claim 1 to a patient in need thereof.

18. A method of treating an autoimmune disease, the method comprising administering an effective amount of the recombinant human cytolytic fusion protein (hCFP) according to claim 1 to a patient in need thereof.

19. A method of a treating tissue rejection reaction, the method comprising administering an effective amount of the recombinant human cytolytic fusion protein (hCFP) according to claim 1 to a patient in need thereof.

20. A method of treating a chronic inflammatory disease, the method comprising administering an effective amount of the recombinant human cytolytic fusion protein (hCFP) according to claim 1 to a patient in need thereof.

\* \* \* \* \*